(12) United States Patent
Assmann et al.

(10) Patent No.: US 6,310,005 B1
(45) Date of Patent: Oct. 30, 2001

(54) ISOTHIAZOLE CARBOXYLIC ACID AMIDES

(75) Inventors: Lutz Assmann, Langenfeld; Hans-Ludwig Elbe, Wuppertal; Dietmar Kuhnt, Burscheid; Gerd Hänssler, Leverkusen; Karl-Heinz Kuck, Langenfeld, all of (DE); Yoshinori Kitagawa, Tochigi (JP); Haruko Sawada, Ibaraki (JP); Haruhiko Sakuma, Tochigi (JP)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/787,056

(22) PCT Filed: Sep. 9, 1999

(86) PCT No.: PCT/EP99/06649

§ 371 Date: Mar. 13, 2001

§ 102(e) Date: Mar. 13, 2001

(87) PCT Pub. No.: WO00/15622

PCT Pub. Date: Mar. 23, 2000

(30) Foreign Application Priority Data

Sep. 16, 1998 (DE) .............................................. 198 42 354

(51) Int. Cl.$^7$ ...................... C07D 275/03; A01N 43/80
(52) U.S. Cl. ................ 504/223; 504/226; 504/266; 504/269; 544/65; 544/133; 548/187; 548/213
(58) Field of Search .................... 548/213, 187; 544/65, 133; 504/226, 223, 266, 269

(56) References Cited

U.S. PATENT DOCUMENTS 5,240,951   8/1993   Shimotori et al. ................... 514/372

FOREIGN PATENT DOCUMENTS 1770976   1/1972   (DE) .
313091    4/1989   (EP) .
99/24413  5/1999   (WO) .

OTHER PUBLICATIONS

Chemical Abstracts, vol. 119, No. 11, Sep. 13, 1993, Columbus, Ohio, US; Abstract No. 117242x, Seite 933, XP002126109, Zusammenfassung & JP 05–059024 A (Mitsui Toatsu Chemicals) Mar. 9, 1993.

Chemical Abstracts, vol. 120, No. 21, May 23, 1994, Columbus, Ohio, US; Seite 398, XP002126110, Zusammenfassung & JP 06–009313 A (Mitsui Toatsu Chemicals) Jan. 18, 1994, in der Anmeldung erwähnt.

*Primary Examiner*—Robert Gerstl
(74) *Attorney, Agent, or Firm*—Joseph C. Gil; Jackie Ann Zurcher

(57) ABSTRACT

Novel isothiazolecarboxamides of the formula

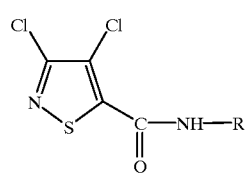

(I)

in which

R is as defined in the description, a plurality of processes for preparing the novel compounds and their use for protecting plants against attack by undesirable microorganisms.

9 Claims, No Drawings

ISOTHIAZOLE CARBOXYLIC ACID AMIDES

FIELD OF THE INVENTION

The present invention relates to novel isothiazolecarboxamides, to a plurality of processes for their preparation and to their use for protecting plants against attack by undesirable microorganisms and animal pests.

BACKGROUND OF THE INVENTION

It is already known that numerous isothiazolecarboxylic acid derivatives have fungicidal properties (of U.S. Pat. No. 5,240,951 and JP-A 06-009 313). Thus, for example, N-furfuryl-3,4-dichloro-isothiazole-5-carboxamide and N-morpholinyl-3,4-dichloro-isothiazole-5-carboxamide can be employed for controlling fungi. The activity of these compounds is good, but in some cases leaves something to be desired at low application rates.

SUMMARY OF THE INVENTION

Isothiazolecarboxamides of the formula

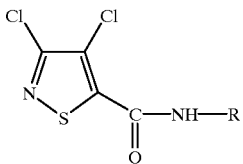

may be used for protecting plants against attack by undesirable micoorganisms and animal pests.

DETAILED DESCRIPTION

This invention, accordingly, provides novel isothiazolecarboxamides of the formula

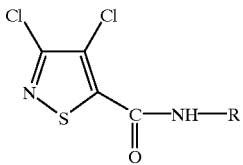 (I)

in which

R represents optionally substituted heterocyclyl-alkyl or represents a radical of the formula

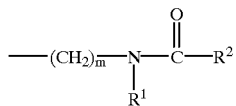

in which $R^1$ represents hydrogen or alkyl, $R^2$ represents alkoxy or represents optionally substituted heterocyclyl and m represents integers from 1 to 4, or R represents a radical of the formula

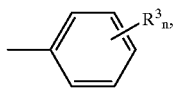

in which $R^3$ represents optionally substituted heterocyclyl or represents a radical of the formula

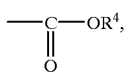

in which $R^4$ represents cycloalkyl, and n represents 1 or 2, or

R represents morpholinyl, piperazinyl, pyrazolyl, imidazolyl, 1,2,4-triazolyl,pyrrolyl, thienyl, thiazolyl, isothiazolyl, oxazolyl, isoxazolyl, pyridinyl, pyrimidinyl, triazinyl, 1,2,3-triazolyl, tetrazolyl, benzotriazolyl, quinolinyl, isoquinolinyl, quinazolinyl, indolyl, benzothienyl, benzofuranyl, benzothiazolyl or benzimidazolyl, where these radicals can be mono- or disubstituted by identical or different substituents from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy.

Furthermore, it has been found that isothiazolecarboxamides of the formula (1) are obtained when a) 3,4-dichloro-isothiazole-5-carbonyl chloride of the formula

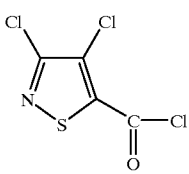 (II)

is reacted with amines of the formula

 (III)

in which

R is as defined above, if appropriate in the presence of an acid binder and if appropriate in the presence of a diluent, or b) 3,4-dichloro-isothiazole-5-carboxamide of the formula

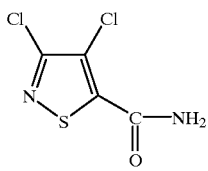

(IV)

is reacted with hydroxyl compounds of the formula

HO—A—X        (V)

in which
X represents optionally substituted heterocyclyl or a radical of the formula

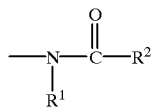

in which
R$^1$ and R$^2$ are each as defined above, and
A represents optionally branched alkylene or (CH$_2$)$_m$, in the presence of a diluent and in the presence of a dehydrating agent.

Finally, it has been found that the isothiazolecarboxamides of the formula (I) are highly suitable for protecting plants against attack by undesirable microorganisms. The compounds according to the invention are suitable both for mobilizing defenses of the plants against attack by undesirable microorganisms and as microbicides for the direct control of the microorganisms.

Surprisingly, the compounds according to the invention have better microbicidal activity than N-furfuryl-3,4-dichloro-isothiazole-5-carboxamide and N-morpholinyl-3,4-dichloro-isothiazole-5-carboxamide, which are constitutionally similar prior-art active compounds of the same direction of action.

The formula (I) provides a general definition of the isothiazolecarboxamides according to the invention.

R preferably represents optionally benzo-fused five- or six-membered heterocyclylalkyl having 1 to 3 hetero atoms, such as nitrogen, oxygen and/or sulfur, in the heterocyclyl moiety and 1 to 4 carbon atoms in the alkyl moiety, where the heterocyclyl moiety may also contain a carbonyl group or a thiocarbonyl group and may furthermore be mono- or disubstituted by identical or different substituents from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy.

R furthermore preferably represents a radical of the formula

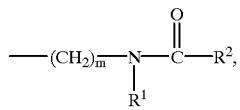

in which
R$^1$ preferably represents hydrogen or alkyl having 1 to 6 carbon atoms,
R$^2$ preferably represents alkoxy having 1 to 6 carbon atoms, or represents five- or six-membered heterocyclyl having 1 to 3 hetero atoms, such as nitrogen, oxygen and/or sulfur, where the heterocyclyl moiety may be mono- or disubstituted by identical or different substituents from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy and
m represents the numbers 1, 2 or 3.

R furthermore preferably represents a radical of the formula

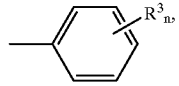

in which
R$^3$ preferably represents five- or six-membered heterocyclyl having 1 to 3 hetero atoms, such as nitrogen, oxygen and/or sulfur, where the heterocyclyl moiety may be mono- or disubstituted by identical or different substituents from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or
R$^3$ represents a radical of the formula

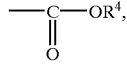

in which
R$^4$ preferably represents cycloalkyl having 3 to 7 carbon atoms, and

R furthermore preferably represents morpholinyl, piperazinyl, pyrazolyl, imidazolyl, 1,2,4triazolyl, pyrrolyl, thienyl, thiazolyl, isothiazolyl, oxazolyl, isoxazolyl, pyridinyl, pyrimidinyl, triazinyl, 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be mono- or disubstituted by identical or different substituents from the group consisting of fluorine, chlorine, bromine, cyano, nitro, carboxyl, methyl, ethyl, propyl, isopropyl, n-butyl, sec-butyl, iso-butyl, tert-butyl, balogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and/or phenoxy.

R particularly preferably represents a radical of the formula

—$A^1$—$R^5$, in which $A^1$ represents —$CH_2$—, —$CH_2$—$CH_2$— or

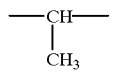

and $R^5$ represents thiazolidinethion-3-yl, morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl, 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be mono- or disubstituted by identical or different substituents from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy.

R furthermore particularly preferably represents a radical of the formula

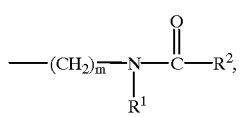

in which $R^1$ represents hydrogen or alkyl having 1 to 4 carbon atoms, $R^2$ represents alkoxy having 1 to 4 carbon atoms or represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl or 1,2,3-triazolyl, where these radicals may be mono- or disubstituted by identical or different substituents from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, and m represents 1 or 2.

R furthermore particularly preferably represents a radical of the formula

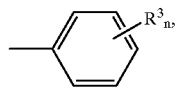

in which $R^3$ represents a heterocycle of the formula

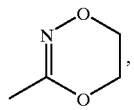

represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl or 1,2,3-triazolyl, where these radicals may be mono- or disubstituted by identical or different substituents from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy or $R^3$ represents a radical of the formula

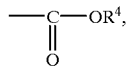

in which $R^4$ represents cyclopropyl, cyclopentyl or cyclohexyl, and n represents 1 or 2.

R furthermore particularly preferably represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl, 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be mono- or disubstituted by identical or different substituents from the group consisting of fluorine, chlorine, bromine, cyano, nitro, carboxyl, methyl, ethyl, trifluoromethyl, difluoromethyl, trichloromethyl, methoxycarbonyl, ethoxycarbonyl, methoxy, ethoxy, trifluoromethoxy, methylthio, trifluoromethylthio, methylamino, dimethylamino, phenyl and phenoxy.

R very particularly preferably represents a radical of the formula

—$A^1$—$R^5$, in which $A^1$ represents —$CH_2$—, —$CH_2$—$CH_2$— or

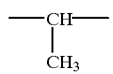

and $R^5$ represents thiazolidinethion-3-yl, morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl, 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be mono- or disubstituted by identical or different substituents from the group consisting of fluorine, chlorine, bromine, cyano, nitro, carboxyl, methyl, ethyl, trifluoromethyl, difluoromethyl, trichloromethyl, methoxycarbonyl, ethoxycarbonyl, methoxy, ethoxy, trifluoromethoxy, methylthio, trifluoromethylthio, methylamino, dimethylamino, phenyl and phenoxy.

R furthermore very particularly preferably represents a radical of the formula

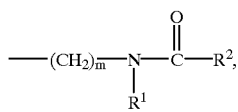

in which
  $R^1$ represents hydrogen, methyl or ethyl,
  $R^2$ represents methoxy, ethoxy or isopropoxy or
  $R^2$ represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl, 1,2,3-triazolyl, where these radicals may be mono- or disubstituted by identical or different substituents from the group consisting of fluorine, chlorine, bromine, cyano, nitro, carboxyl, methyl, ethyl, trifluoromethyl, difluoromethyl, trichloromethyl, methoxycarbonyl, ethoxycarbonyl, methoxy, ethoxy, trifluoromethoxy, methylthio, trifluoromethylthio, methylamino, dimethylamino, phenyl and phenoxy, and
  m represents 1 or 2.

R furthermore very particularly preferably represents a radical of the formula

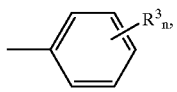

in which
  $R^3$ represents a heterocycle of the formula

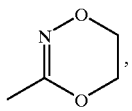

represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl or 1,2,3-triazolyl, where these radicals may be mono- or disubstituted by identical or different substituents from the group consisting of fluorine, chlorine, bromine, cyano, nitro, carboxyl, methyl, ethyl, trifluoromethyl, difluoromethyl, trichloromethyl, methoxycarbonyl, ethoxycarbonyl, methoxy, ethoxy, trifluoromethoxy, methylthio, trifluoromethylthio, methylamino, dimethylamino, phenyl and phenoxy, or
  $R^3$ represents a radical of the formula

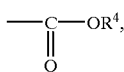

in which
  $R^4$ represents cyclopentyl or cyclohexyl and
  n represents 1 or 2.

R furthermore very particularly preferably represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl or 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be mono- or disubstituted by identical or different substituents from the group consisting of fluorine, chlorine, bromine, cyano, nitro, methyl, trifluoromethyl, methoxycarbonyl, methoxy, trifluoromethoxy, methylthio and trifluoromethylthio.

The above substituent definitions can be combined among each other in any desired manner. Additionally, individual definitions may be redundant.

Using 3,4-dichloro-isothiazole-5-carbonyl chloride and 4-aminomorpholine as starting materials, the course of the process (a) according to the invention can be illustrated by the equation below.

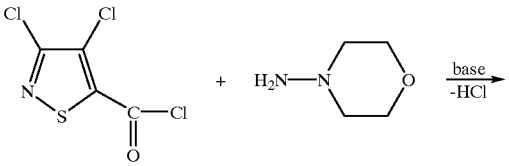

-continued

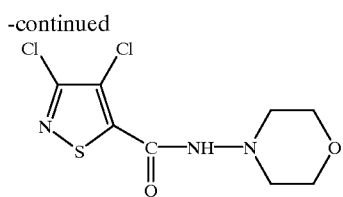

Using 3,4-dichloro-isothiazole-5-carboxamide and 3-hydroxymethyl-thiazolidine-2-thione as starting materials, the course of the process (b) according to the invention can be illustrated by the equation below.

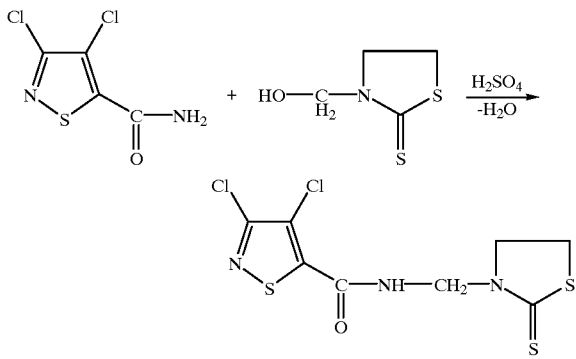

The 3,4-dichloro-isothiazole-5-carbonyl chloride of the formula (II) required as starting material for carrying out the process (a) according to the invention is known (cf. U.S. Pat. No. 5,240,951).

The formula (III) provides a general definition of the amines furthermore required as reaction components for carrying out the process (a) according to the invention. In this formula, R preferably has those meanings which have already been mentioned in connection with the description of the compounds of the formula (I) according to the invention as being preferred for this radical.

The amines of the formula (III) are known or can be prepared by known methods.

Suitable acid binders for carrying out the process (a) according to the invention are all customary inorganic or organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate, furthermore ammonium hydroxide, ammonium acetate or ammonium carbonate, or tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclo-octane (DABCO), diazabicyclononene (DBN) or diazabicycloundecene (DBU).

Suitable diluents for carrying out the process (a) according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichlorethane or trichloroethane; ethers, such as diethyl ether, diisopropyl ether, methyl-t-butyl ether, methyl-t-amyl ether, dioxane, tetrahydrofuran, 1,2-dimethoxyethane, 1,2-diethoxyethane or anisole; nitrites, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric acid triamide; esters such as methyl acetate or ethyl acetate; sulfoxides, such as dimethylsulfoxide; sulfones, such as sulfolane.

When carrying out the process (a) according to the invention the reaction temperatures can be varied within a relatively wide range. In general, the reaction is carried out at temperatures between −10° C. and +150° C., preferably between 0° C. and 100° C.

The process (a) according to the invention is generally carried out under atmospheric pressure. However, it is also possible to operate under elevated or, if no volatile components take part in the reaction, under reduced pressure.

When carrying out the process (a) according to the invention, generally 1 to 5 mol, preferably 1 to 2 mol, of amine of the formula (m) and an equivalent amount or an excess of acid binder are employed per mole of 3,4-dichloro-isothiazole-5-carbonyl chloride of the formula (II). Work-up is carried out by customary methods. In general, the reaction mixture is concentrated after the reaction has ended, the residue that remains is admixed with water and an organic solvent which is sparingly miscible with water, the organic phase is separated off, washed, dried and concentrated. The product that remains can be freed of any impurities that may be present by customary methods.

The 3,4-dichloro-isothiazole-5-carboxamide of the formula (IV) required as starting material for carrying out the process (b) according to the invention is known (cf. U.S. Pat. No. 5,240,951).

The formula (V) provides a general definition of the hydroxyl compounds furthermore required as reaction components for carying out the process (b) according to the invention. In this formula X preferably represents optionally benzo-fused five- or six-membered heterocyclyl having 1 to 3 hetero atoms, such as oxygen, nitrogen and/or sulfur, where the heterocycle may also contain a carbonyl group or a thiocarbonyl group and may furthermore be mono- or disubstituted by identical or different substituents from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy.

X furthermore preferably represents a radical of the formula

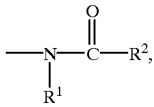

in which $R^1$ and $R^2$ preferably have those meanings which have been mentioned in connection with the description of the substances of the formula (I) according to the invention as being preferred for these radicals.

A preferably represents straight-chain or branched alkylene having 1 to 4 carbon atoms.

X particularly preferably represents thiazolidinethion-3-yl, morpholinyl, piperazinyl, pyrazolyl, imidazolyl, 1,2,4triazolyl, pyrrolyl, thienyl, thiazolyl, isothiazolyl, oxazolyl, isoxazolyl, pyridinyl, pyrimidinyl, triazinyl, 1,2,3-triazolyl, benzotriazolyl, quinolinyl, isoquinolinyl, quinazolinyl, indolyl, benzothienyl, benzofiranyl, benzothiazolyl or benzimidazolyl, where these radicals may be mono- or disubstituted by identical or different substituents from the group consisting of fluorine, chlorine, bromine, cyano, nitro, carboxyl, methyl, ethyl, propyl, isopropyl, n-butyl, sec-butyl, iso-butyl, tert-butyl, halogenoalkyl halogenoalkyl having 1 to 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 to 2 carbon atoms and 1 to 3 fluorine, chlorine and/or bromine atoms, methylthio, ethylthio, halogenoalkylthio having 1 to 2 carbon atoms and 1 to 3 fluorine, chlorine and/or bromine atoms, metbylamino, ethylamino, dimethylamino, diethylamino, phenyl and phenoxy.

X furthermore particularly preferably represents a radical of the formula

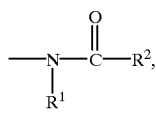

in which
$R^1$ and $R^2$ have those meanings which have been mentioned in connection with the description of the substances of the formula (I) according to the invention as being particularly preferred for these radicals.

A particularly preferably represents $CH_2$—, —$CH_2$—$CH_2$— or

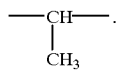

X very particularly preferably represents thiazolidinethion-3-yl, morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl, 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be mono- or disubstituted by identical or different substituents from the group consisting of fluorine, chlorine, bromine, cyano, nitro, carboxyl, methyl, ethyl, trifluoromethyl, difluoromethyl, trichloromethyl, methoxycarbonyl, ethoxycarbonyl, methoxy, ethoxy, trifluoromethoxy, methylthio, trifluoromethyltbio, methylamino, dimethylamino, phenyl and phenoxy.

X furthermore very particularly preferably represents a radical of the formula

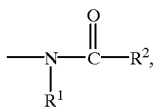

in which
$R^1$ and $R^2$ have those meanings which have been mentioned in connection with the description of the substances of the formula (I) according to the invention as being very particularly preferred for these radicals.

A very particularly preferably represents $CH_2$—, —$CH_2$—$CH_2$— or

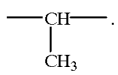

The hydroxyl compounds of the formula (V) are known or can be prepared by known methods.

Suitable diluents for carrying out the process (b) according to the invention are all inert organic solvents which are customary for such reactions. Preference is given to using glacial acetic acid.

Suitable dehydrating agents for carrying out the process (b) according to the invention are all customary reagents which are capable of dehydration. Preference is giving to using acids, such as sulphuric acid or p-toluenesulphonic acid, and also drying agents, such as anhydrous silica gel.

When carrying out the process (b) according to the invention, the reaction temperatures can again be varied within a relatively wide range. In general, the reaction is carried out at temperatures between 0° C. and 150° C., preferably between 10° C. and 130° C.

The process (b) according to the invention is likewise generally carried out under atmospheric pressure. However, it is also possible to carry out the process under elevated or reduced pressure.

When carrying out the process (b) according to the invention, generally 1 to 2 mol, preferably 1 to 1.5 mol, of hydroxyl compound of formula (V) and 2 to 6 mol of dehydrating agent are employed per mole of 3,4-dichloro-isothiazole-5-carboxamide of the formula (IV). Work-up is carried out by customary methods. In general, the reaction mixture is admixed with water and then extracted with an organic solvent which is sparingly miscible with water, and the combined organic phases are dried and concentrated under reduced pressure. The product that remains can be freed of any impurities that may still be present by customary methods.

The active compounds according to the invention have a strong plant-strengthening activity in plants. They are therefore suitable for mobilizing the defences of the plant against attack by undesirable microorganisms.

In the present context, plant-strengthening (resistance-inducing) compounds are compounds which are capable of stimulating the defensive system of plants in such a way that the treated plants, when subsequently inoculated with undesirable microorganisms, develop substantial resistance against these microorganisms.

In the present case, undesirable microorganisms are phytopathogenic fungi, bacteria and viruses. The compounds according to the invention can thus be employed to protect plants for a certain period of time after the treatment against the attack by the abovementioned harmful organisms. The period of time for which protection is provided generally extends from 1 to 10 days, preferably from 1 to 7 days, after the treatment of the plants with the active compounds.

In addition to the plant-strengthening (resistance-inducing) activity, the active compounds according to the invention also have strong microbicidal activity and are additionally employed in practice for the direct control of undesirable microorganisms. The active compounds are suitable for use as crop protection agents, in particular as fungicides.

In crop protection, the undesirable microorganisms include fungi from the classes of the Plasmodiophoromycetes, Oomycetes, Chytridiomycetes, Zygomycetes, Ascomycetes, Basidiomycetes, Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, Peronospora pisi or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, Pyrenophora teres or *Pyrenophora graminea* (conidia form: Drechslera, syn.: Helminthosporium);

Cochliobolus species, such as, for example, *Cochliobolus sativus* (conidia form: Drechslera, syn.: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, Ustilago nuda or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The good crop safety of the active compounds at the concentrations necessary for controlling plant diseases permits a treatment of above-ground parts of plants, and also a treatment of vegetative propagation stock and seed and of the soil.

The active compounds according to the invention can be used here particularly successfully for controlling cereal diseases, such as, for example, against Erysiphe species, or of diseases in viticulture and in fruit and vegetable growing, such as, for example, against Plasmopara or Venturia species, or of rice diseases, such as, for example, against Pyricularia species. Other plant diseases, such as, for example, Septoria, Cochliobolus, Pyrenophora and Pseudocercosporella species, can also be controlled successfully with the active compounds according to the invention, and specific mention may be made of *Drechslera teres.*

The active compounds according to the invention are also suitable for increasing the harvest yield. Additionally, they have reduced toxicity and good crop safety.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam fonners are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolyzates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components. Examples of co-components in mixtures are the following compounds:

Fungicides:

aldimorph, ampropylfos, ampropylfos potassium, andoprim, anilazine, azaconazole, azoxystrobin, benalaxyl, bendicar, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminum, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), quinoxyfen, sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[(1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorobenyl)-3-phenyloxiranyl]-methyl]-1H-1,2,4-triazole, 1-[1-[2-[(2,4-dicblorophenyl)-methoxy]-phenyl]-ethenyl]-1H-imidazole, 1-methyl-5-nonyl-2-(phenylmethyl)-3-pyrrolidinole, 2',6'-dibromo-2-methyl -4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl 1,3,4-thiadiazole, 2-[[6-deoxy-4-O-(4-O-methyl-β-D-glycopyranosyl)-a-D-glucopyranosyl]-amino]-4 -methoxy-1H-pyolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione,
3,5-dichloro-N-[cyano-[(1-methyl-2-propinyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methaneamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethylmorpholinehydrochloride,
ethyl [(4-chlorophenyl)-azo]-cyanoacetate,
potassium hydrogen carbonate,
methanetetrathiol sodium salt,
methyl 1-(2,3-dihydro2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide.
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidinearnine,
N-(5-chloro-2-methylphenyl)-2-methoxy-N-(2-oxo-3-oxazolidinyl)-acetamide,
N-(6-methoxy)-3-pyridinyl)-cyclopropanecarboxanide,
N-[2,2,2-trichloro-1-[(chloroacetyl)-amino]-ethyl]-benzamide,
N-[3-chloro-4,5-bis-(2-propinyloxy)-phenyl]-N'-methoxy-methaneimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one.

Bactericides:
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypernethrin, alphamethrin, amitraz, avermectin, AZ 60541, azadirachtin, azamethiphos, azinphos A, azinphos M, azocyclotin, Bacillus popilliae, Bacillus sphaericus, Bacillus subtilis, Bacillus thuringiensis, baculoviruses, Beauveria bassiana, Beauveria tenella, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, cblorfluazuron, chlormephos, chlorpyrifos, chlorpyrifos M, chlovaphorthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton S-methyl, diafenthiuron, diazinon, dichlorvos, diflubenzuron, dimethoate, dimethylvinphos, diofenolan, disulfoton, docusat-sodium, dofenapyn, elfusilanate, emamectin, empenthrin, endosulfan, Entomopfthora spp., esfenvalerate, ethiofencarb, ethion, ethoprophos, etofenprox, etoxazole, etrimphos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazophos, isofenphos, isoxathion, ivermectin, nuclear polyhedrosis viruses, lambda-cyhalothrin, lufenuron, malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M, Paecilomyces fumosoroseus, parathion A, parathion M, permethrin, phenthoate, phorate, phosalone, phosmet, phosphamidon, phoxim, pirimicarb, pirimiphos A, pirimiphos M, profenofos, promecarb, propoxur, prothiophos, prothoate, pymetrozine, pyraclofos, pyresmethrin, pyrethrum, pyridaben, pyridathione, pyrimidifen, pyriproxifen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, Verticillium lecanii.
YI 5302
zeta-cypermethrin, zolaprofos,
(1R-cis)-[5-phenylmethyl)-3-furanyl]-methyl 3-[(dihydro-2-oxo-3(2H)-furanylidene)-methyl]-2,2-dimethylcyclopropanecarboxylate,
(3-phenoxyphenyl)-methyl 2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-docecyl-1,4-naphthalenedione, 2-chloro-N-[[[4-(1-phenylethoxy)-phenyl]-amino]- carbonyl]-benzamide, 2-chloro-N-[[[4(2,2-dichloro 1,1-difluoroethoxy)- phenyl]-amino]-carbonyl]-benzamide, 3-methylphenyl propylcarbamate, 4-[4-(4-ethoxyphenyl)-4-methylpentyl]-1-fluoro-2- phenoxy-benzene, 4-chloro-2-(1,1-dimethylethyl)-5-[[2-(2,6-dimethyl-4 -phenoxyphenoxy)ethyl]thio]-3(2H)-pyridazinone, 4-chloro-2-(2-chloro-2-methylpropyl)-5-[(6-iodo-3- pyridinyl)methoxy]-3(2H)-pyridazinone, 4-chloro-5[(6-chloro-3-pyridinyl)methoxy]-2-(3,4- dichlorophenyl-3(2H)-pyridazinone, Bacillus thuringiensis strain EG-2348, (2-benzoyl-1-(1,1-dimethylethyl)-hydrazinobenzoic acid, 2,2-dimethyl-3-(2,4-dichlorophenyl)-2-oxo-1-oxaspiro [4.5]dec-3-en-4-yl butanoate,

[3-[(6-chloro-3-pyridinyl)methyl]-2-thiazolidinylidene]- cyanamide, dihydro-2-(nitromethylene)-2H-1,3-thiazine-3-(4H)- carboxaldehyde, ethyl-[2-[[1,6-dihydro-6-oxo-1-(phenylmethyl)-4- pyridazinyl]oxy]ethyl]-carbamate, N-(3,4,4-trifluoro-1-oxo-3-butenyl)-glycine, N-(4-chlorophenyl)-3-[4-difluoromethoxy)phenyl]-4,5- dihydro4-phenyl-1H-pyrazole-1-carboxamide, N-[(2-chloro-5-thiazolyl)methyl]-N'-methyl-N"-nitro- guanidine, N-methyl-N'-(1-methyl-2-propenyl) 1,2- hydrazinedicarbothioamide, N-methyl-N'-2-propenyl-1,2-hydrazinedicarbothioamide, O,O-diethyl[2-(dipropylamino)-2-oxoethyl]- ethylphosphoramideothioate.

It is also possible to admix other known active compounds, such as herbicides, or else fertilizers and growth-promoting substances.

The active compounds can be used as such, in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When using the active compounds according to the invention for controlling microorganisms, the application rates can be varied within a relatively wide range, depending on the kind of application. When treating parts of plants, the active compound application rates are generally between 0.1 and 10,000 g/ha, preferably between 10 and 1000g/ha. When treating seed, the active compound application rates are generally between 0.001 and 50 g per kilogram of seed, preferably between 0.01 and 10 g per kilogram of seed. When treating the soil, the active compound application rates are generally between 0.1 and 10,000 g/ha, preferably between 1 and 5000 g/ha.

When used against animal pests, the compounds according to the invention may also be present in commercial formulations and in the use forms prepared from these formulations as a mixture with synergists. Synergists are compounds which increase the activity of the active compounds, without it being necessary for the synergist which is added to be active itself.

The active compound content of the use forms prepared from the commercial formulations can vary within wide ranges. The active compound concentration of the use form may be from 0.0000001 to 95% by weight of active compound, preferably between 0.0001 and 1% by weight.

Application is carried out in a manner adapted to the use forms.

The preparation and the use of the active compounds according to the invention is illustrated by the examples below.

PREPARATION EXAMPLES

Example 1

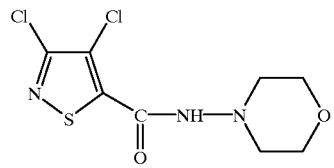

At 0 to 5° C. and with ice-cooling and stirring, 2.43 g (0.01 mol) of 3,4-dichloro-isothiazole-5-carbonyl chloride are added dropwise over a period of 5 minutes to a mixture of 1.21 g (0.011 mol) of 4-amino-morpholine and 22 ml of absolute pyridine. After the addition, the reaction mixture is admixed with 1.5 ml of absolute tetrahydrofuran, allowed to warm to room temperature and then stirred at room temperature for one hour. The reaction mixture is subsequently concentrated under reduced pressure. The residue that remains is admixed with 60 ml of water and 60 ml of ethyl acetate. The organic phase is separated off and the aqueous phase is extracted twice more with ethyl acetate. The combined organic phases are successively washed with 20 ml of saturated aqueous sodium bicarbonate solution and 50 ml of water, then dried over sodium sulphate and concentrated under reduced pressure. The residue is triturated in a mixture of 30 ml methylene chloride and 70 ml of petroleum ether. The resulting solid is filtered off with suction and dried. In this manner, 1.79 g (63% of theory) of N-morpholinyl-3,4-dichloro-isothiazole-5-carboxamide are obtained in the form of a solid of melting point 198 to 199° C.

Example 2

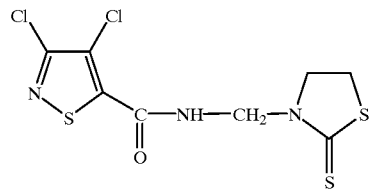

At room temperature, 2.3 g (0.015 mol) of 3-hydroxymethyl-thiazolidine-2-thione are added with stirring to a mixture of 3.0 g (0.015 mol) of 3,4-dichloro-isothiazole-5-carboxamide and 22.5 ml of glacial acetic acid. At room temperature, 3.27 g (0.033 mol) of concentrated sulphuric acid are then added dropwise with stirring, the reaction mixture being cooled with ice. The reaction mixture is first stirred at room temperature for 21 hours then admixed with 5 ml of glacial acetic acid and stirred for a further 3 hours at room temperature. The mixture is admixed with 25 ml of water with ice-cooling and the resulting solid is filtered off. The filter residue is washed with 10 ml of water and 20 ml of petroleum ether, then dissolved in methylene chloride and chromatographed over silica gel using the mobile phase methylene chloride. Concentration of the eluate under reduced pressure gives 0.24 g (5% of theory) of thiazolidine-2-thion-3-yl-methyl-3,4-dichloro-isothiazole-5-arboxamide in the form of a solid of melting point 181 to 182° C.

The isothiazole-carboxamides of the formula (I) listed in the Table below are also prepared by the abovementioned methods.

TABLE 1

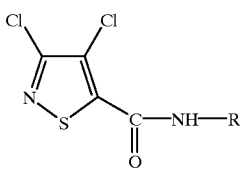

(I)

| Example No. | R | Melting point (° C.) |
|---|---|---|
| 3 | —CH₂—NH—C(=O)— (3,4-dichloroisothiazol-5-yl) | 178–179 |
| 4 | —CH₂—N(CH₃)—C(=O)—OCH₃ | 98–99 |
| 5 | 3-methylphenyl-1,3-dioxazine | 135–138 |
| 6 | 2-methylphenyl-1,3-dioxazine | 160–162 |
| 7 | 3-methylphenyl-C(=O)—O-cyclohexyl | 119–122 |
| 8 | 2-methylphenyl-C(=O)—O-cyclohexyl | 100–102 |

TABLE 1-continued (I)

| Example No. | R | Melting point (° C.) |
|---|---|---|
| 9 | 4-methylphenyl-1,3-dioxazine | 185–187 |
| 10 | 4-methylphenyl-C(=O)—O-cyclohexyl | 144–147 |

Use Example

Example A

Erysiphe Test (Barley)/Induction of Resistance

| Solvent: | 50 parts by weight of N,N-dimethylformamide |
| Emulsifier: | 1.17 parts by weight of alkylaryl polyglycol ether |

To produce a suitable preparation of active compound, 1 part by weight of active compound is mixed with the stated amount of solvent, and the concentrate is diluted with water and the stated amount of emulsifer to the desired concentration.

To test for resistance-reducing activity, young cereal plants are sprayed with the preparation of active compound at the stated application rate. 4 days after the treatment, the plants are inoculated with spores of Erysiphe graminis f. sp. hordei. The plants are subsequently placed in a greenhouse at 70% relative atmospheric humidity and a temperature of 18° C.

Evaluation is carried out 7 days after the inoculation. 0% means an efficacy which corresponds to that of the control, while an efficacy of 100% means that no infection is observed.

Active compounds, application rates and tests results are shown in the Table below.

TABLE A

Erysiphe Test (Barley)/Induction of resistance

| Active compound | Application rate of active compound in g/ha | Efficacy in % |
|---|---|---|
| According to the invention: | | |
| 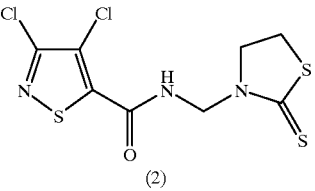 (2) | 750 | 90 |
| 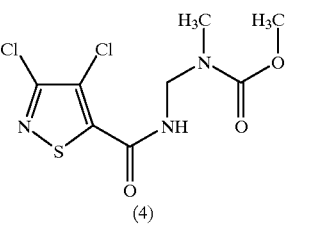 (4) | 750 | 80 |
| 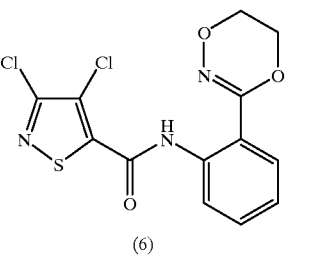 (6) | 750 | 95 |
| 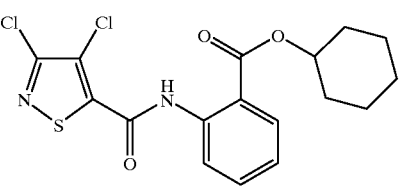 (8) | 750 | 95 |

Example B

Erysiphe Test (Barley)/Induction of Resistance

| | |
|---|---|
| Solvent | 97.6 parts by weight of N,N-dimethylformamide |
| Emulsifier: | 2.4 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for resistance-reducing activity, young cereal plants are sprayed with the preparation of active compound at the stated application rate. 4 days after the treatment, the plants are inoculated with spores of Erysiphe graminis f. sp. hordei. The plants are subsequently placed in a greenhouse at 70% relative atmospheric humidity and a temperature of 18° C.

Evaluation is carried out 7 days after the inoculation. 0% means an efficacy which corresponds to that of the control, while an efficacy of 100% means that no infection is observed.

Active compounds, application rates and test results are shown in the Table below.

TABLE B
Erysiphe Test (Barley)/Induction of resistance
| Active compound | Application rate of active compound in g/ha | Efficacy in % |
|---|---|---|
| According to the invention: | | |
| 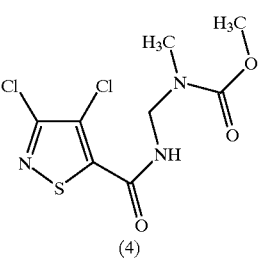 (4) | 375 | 90 |
| 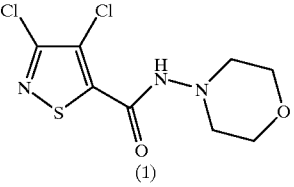 (1) | 375 | 90 |
| 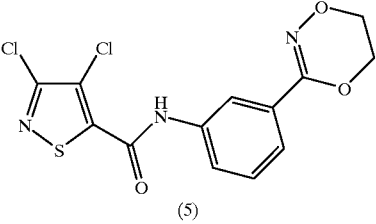 (5) | 375 | 95 |
| 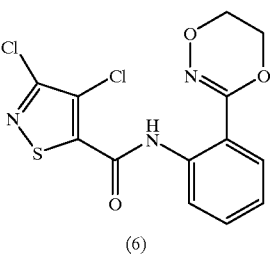 (6) | 375 | 95 |
| 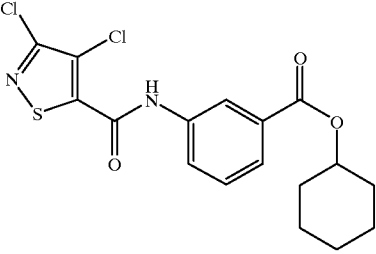 (7) | 375 | 95 |

TABLE B-continued

Erysiphe Test (Barley)/Induction of resistance

| Active compound | Application rate of active compound in g/ha | Efficacy in % |
|---|---|---|
| (8) | 375 | 100 |
| (9) | 375 | 90 |
| (10) | 375 | 95 |

Example C
Pyricularia Test (Rice)/Protective

| | |
|---|---|
| Solvent: | 97.6 parts by weight of N,N-dimethylformamide |
| Emulsifier: | 2.4 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young rice plants are sprayed with the preparation of active compound at the stated application rate. After the spray coating has dried on, the plants are inoculated with an aqueous spore suspension of Pyricularia oryzae and then remain at 100% relative atmospheric humidity and 26° C. for 24 hours. The plants are subsequently placed in a greenhouse at 80% relative atmospheric humidity and a temperature of 26° C.

Evaluation is carried out 7 days after the inoculation. 0% means an efficacy which corresponds to that of the control, while an efficacy of 100% means that no infection is observed.

Active compounds, application rates and test results are shown in the Table below.

TABLE C

Pyricularia Test (Rice)/protective

| Active compound | Application rate of active compound in g/ha | Efficacy in % |
|---|---|---|
| According to the invention: | | |
| (4) | 375 | 70 |

TABLE C-continued

Pyricularia Test (Rice)/protective

| Active compound | Application rate of active compound in g/ha | Efficacy in % |
|---|---|---|
| 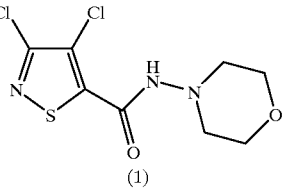 (1) | 375 | 70 |

What is claimed is:

1. An isothiazolecarboxamide of the formula

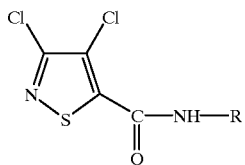 (I)

wherein

R represents a radical of the formula $-A^1-R^5$, wherein $A^1$ represents —CH$_2$—, —CH$_2$—CH$_2$— or

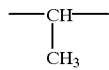

and $R^5$ represents thiazolidinethion-3-yl, morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl, 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be unsubstituted or mono- or disubstituted by identical or different substituents from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, or R represents a radical of the formula

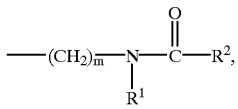

wherein $R^1$ represents hydrogen or alkyl having 1 to 4 carbon atoms, $R^2$ represents alkoxy having 1 to 4 carbon atoms or represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl or 1,2,3-triazolyl, where these radicals may be unsubstituted or mono- or disubstituted by identical or different substituents from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, and m represents 1 or 2, or R represents a radical of the formula

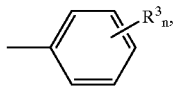

wherein $R^3$ represents a heterocycle of the formula

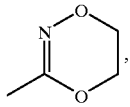

or represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl or 1,2,3-triazolyl, where these radicals may be unsubstituted or mono- or disubstituted by identical or different substituents from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy or $R^3$ represents a radical of the formula

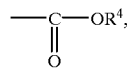

wherein
$R^4$ represents cyclopropyl, cyclopentyl or cyclohexyl, and
n represents 1 or 2, or R represents morpholinyl, piperazinyl, pyrazolyl, imidazolyl, 1,2,4-triazolyl, pyrrolyl, thienyl, thiazolyl, isothiazolyl, oxazolyl, isoxazolyl, pyridinyl, pyrimidinyl, triazinyl, 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be unsubstituted or mono- or disubstituted by identical or different substituents from the group consisting of fluorine, chlorine, bromine, cyano, nitro, carboxyl, methyl, ethyl, trifluoromethyl, difluoromethyl, trichloromethyl, methoxycarbonyl, ethoxycarbonyl, methoxy, ethoxy, trifluoromethoxy, methylthio, trifluoromethylthio, methylamino, dimethylamino, phenyl and phenoxy.

2. A process for preparing an isothiazolecarboxamide of the formula (I) as claimed in claim 1, comprising the step of reacting
a) 3,4-dichloro-isothiazole-5-carbonyl chloride of the formula

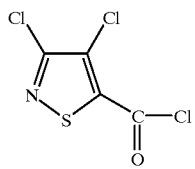

(II)

with an amine of the formula

H$_2$N—R        (III)

wherein
R is as defined in claim 1, or
b) 3,4-dichloro-isothiazole-5-carboxamide of the formula (IV)

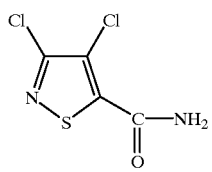

with a hydroxyl compound of the formula

HO—A—X        (V)

wherein
X represents unsubstituted or substituted heterocyclyl or a radical of the formula

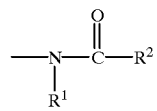

in which
$R^1$ and $R^2$ are each as defined in claim 1, and
A represents unbranched or branched alkylene or (CH$_2$)$_m$, in the presence of a diluent and in the presence of a dehydrating agent.

3. A composition for protecting plants against attack by undesirable microorganisms, comprising one or more isothiazolecarboxamide of the formula (I) as claimed in claim 1, and an ingredient selected from extenders, surfactants and mixtures thereof.

4. A method for protecting plants against attack by undesirable microorganisms, comprising the step of applying one or more isothiazolecarboxamides of the formula (I) as claimed in claim 1 to the plants and/or their habitat.

5. A process for preparing compositions for protecting plants against attack by undesirable microorganisms, comprising the step of mixing one or more isothiazolecarboxamides of the formula (I) as claimed in claim 1 with extenders and/or surfactants.

6. The isothiazolecarboxamide as claimed in claim 1, having the formula

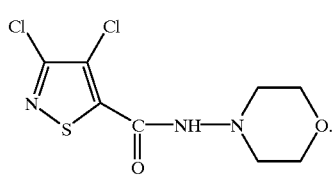

7. The isothiazolecarboxamide as claimed in claim 1, having the formula

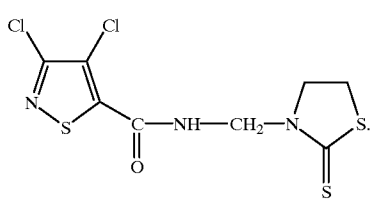

8. The isothiazolecarboxamide as claimed in claim 1, having the formula
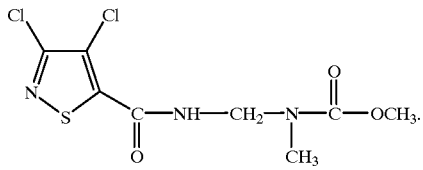
9. The isothiazolecarboxamide as claimed in claim 1, having the formula
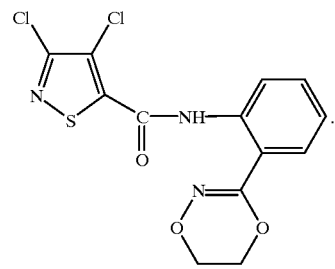
* * * * *